March 24, 1964 R. S. MOORE Plant Pat. 2,385
ROSE
Filed Jan. 12, 1962
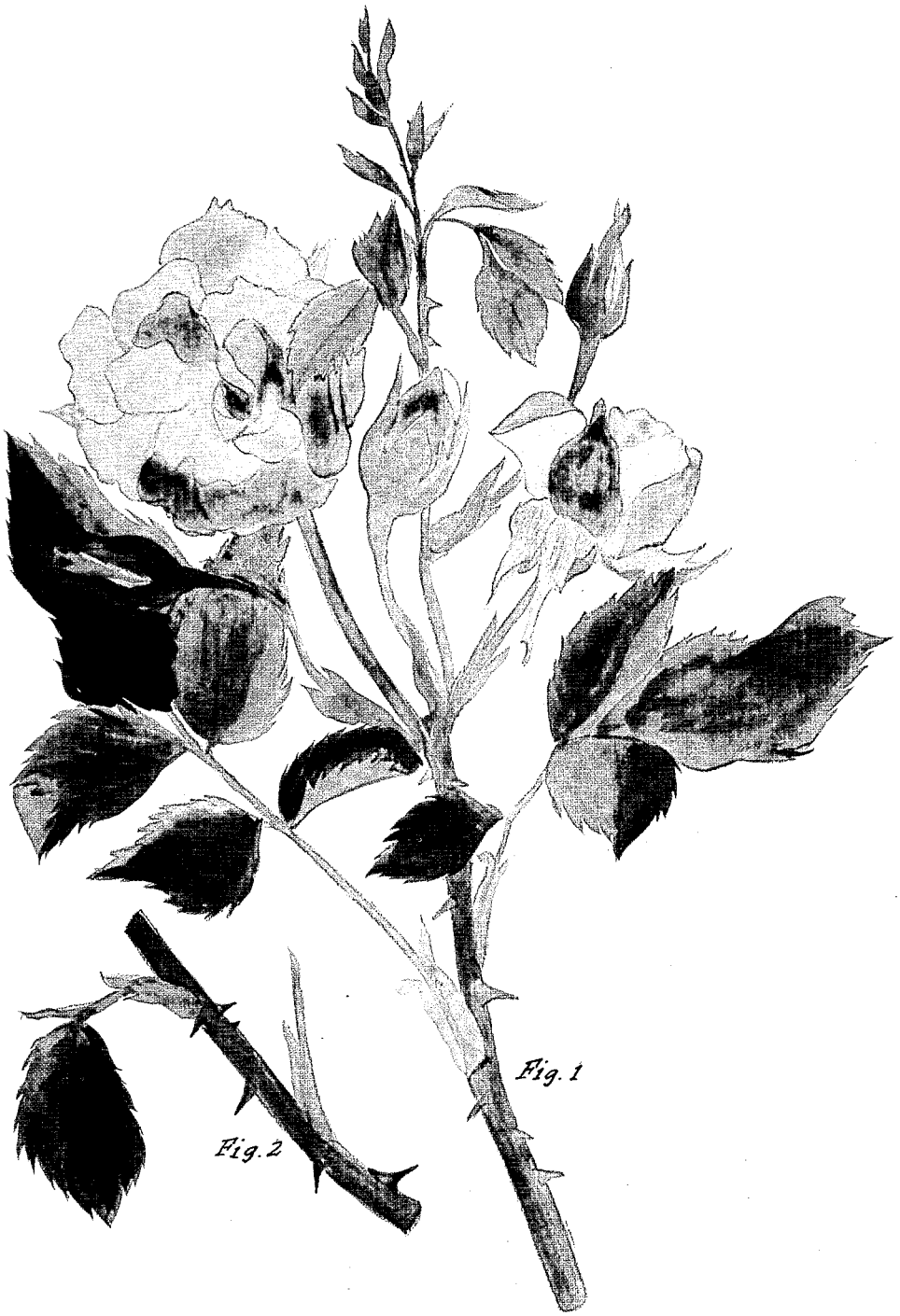
WITNESS
Jeanette Nunn Copley
INVENTOR
RALPH S. MOORE
ATTORNEYS

United States Patent Office

Plant Pat. 2,385
Patented Mar. 24, 1964

2,385
ROSE

Ralph S. Moore, 2519 E. Mineral King, Visalia, Calif.

Filed Jan. 12, 1962, Ser. No. 165,976
1 Claim. (Cl. Plt.—28)

This invention relates to a new and distinct variety of hardy,bush-type floribunda rose plant.

This plant is characterized as to novelty by its exceedingly vigorous, bushy growth and its glossy foliage, together with the bright red color of its abundant flowers.

This new variety may be grown in the garden as a regular floribunda variety or may be planted as a medium tall (four feet) hedge, which hedge requires very little shearing. The flowers are always borne upright on wiry, stiff stems, and are sturdy and dependable in all seasons. In addition, the flowers keep very well when cut.

The bright red shade of the flowers is an attention-getter when the plants are in bloom. The open flowers look somewhat like carnations of the broad petaled type, and the nearly heart-shaped petals are somewhat waved, making the flower look more double than it in fact is.

This variety of floribunda rose plant was originated by me, in my nursery located at Visalia, California, and under conditions of careful control and observation, as a cross between an un-named seedling (polyantha type) as the seed parent and Floradora (unpatented) as the pollen parent. Subsequent to origination of the variety, I successfully asexually reproduced it in my nursery, located as aforesaid, by budding as well as cuttings, the reproductions having run true in all respects.

The drawing illustrates the variety including foliage, buds and flowers.

Referring now sepcifically to the new and distinct variety of floribunda rose plant, the following is a detailed description thereof in outline; all major color plate identifications being to the British Colour Council Horticultural Colour Chart, except where common terms of color definition are employed.

Type: Hardy; bush; outdoor; seedling; cut flowers; garden decoration.

Class: Floribunda.

*Flowers*

Continuity: Intermittent to continuous.

Fragrance: Slight.

Flowers borne: Usually three to five or more to each stem in irregular, rounded clusters, on medium length stems of normal strength.

Quantity of bloom: Free and abundant, outdoors.

Bud:

*Peduncle.*—Short to medium length; medium size; erect, stiff; medium reddish to medium green; almost smooth; few, short, reddish hairs.

*Before calyx breaks.*—Size—medium to small. Form—pointed, with few short foliaceous appendages on the surface of the bud, with foliaceous parts extending beyond the tip of the bud equal to ¼ or more of its length. Color—bronzy green.

*As calyx breaks.*—Color—red.

*As first petal opens.*—Size—medium. Form—pointed, ovoid. Color: outside—Cardinal Red 822/1, with variations both lighter and darker; inside—Cardinal Red 822/2, with variations both lighter and darker. Opening—opens well.

Bloom:

*Size when fully opened.*—Medium, 2" to 2¼".

*Petalage.*—Double; from 20 to 25 petals arranged regularly.

*Form.*—Flat and cupped at first; becoming cupped; petals becoming at maturity very loosely rolled inward.

Petals: Moderately thick; with inside satiny and outside satiny.

*Shape.*—Outside—nearly heart-shaped; intermediate—nearly heart-shaped; inside—obovate.

*Color.*—Newly opened flower from plant grown outdoors (September)—(1) Outside petal: outside surface—Tyrian Rose 24, with both lighter and darker shades; inside surface—with a tip of yellow at base thence into shades of Tyrian Rose and thence into Cardinal Red 822/2 or 822/3. (2) Intermediate petal: outside surface—same as above; inside surface—same as above. (3) Inner petal: outside surface—same as (1) above—Tyrian Rose 24; inside surface—shaded as in (2) above but shading into Crimson 22 instead of Cardinal Red. Rose opened for three days outdoors (September)—Outside petal: outside surface—greenish-yellow at base, thence into shades between Rose Madder 23/2 and Crimson 22/2; inside surface—same as above at base, thence into shades between Rose Madder 23/1 and Crimson 22/2. Inside petal: outside surface—Rose Madder 23/1; inside surface—Crimson 22/1.

*General color effect.*—Newly opened flower—bright red. Flower open three days—bright rose red or deep pink, depending on the weather.

*Behavior.*—Drop off cleanly; color is a deeper red in cooler weather.

*Flower longevity.*—Four to five days or longer on bush in garden (September). Three to four days as cut roses grown outdoors and kept at living room temperatures (August). Three to four days as cut roses grown in greenhouse and kept at living room temperatures (May-June).

Reproductive organs:

*Stamens.*—Of medium number; arranged regularly about pistils.

*Filaments.*—Short to medium in length; white; most with anthers.

*Anthers.*—Small; reddish; all open at once.

*Pollen.*—Of moderate abundance; lemon.

*Pistils.*—Of medium number.

*Styles.*—Fairly even; short to medium length; medium heavy; bunched.

*Stigma.*—White.

*Ovaries.*—All enclosed in calyx.

*Hips.*—None.

*Sepals.*—Of moderate to short length; recurved; yellow green becoming brown.

*Seeds.*—None.

*Plant*

Foliage:

*Leaves.*—Compound of 5 leaflets; normally abundant; of medium size; moderately heavy and glossy.

*Leaflets.*—Shape—lanceolate. Apex—acute. Base—almost round. Margin—serrate.

*Color.*—Mature: upper surface—normal green; under surface—normal green. Young: upper surface—light green; under surface—light green.

*Rachis.*—Of medium weight; upper side grooved and with few, very small hairs and prickles; under side sparsely thorny.

*Stipules.*—Short; of medium width; with short points turning out at an angle of less than 45°.

*Disease.*—Resistant to mildew as compared with other varieties grown under comparable cultural conditions at Visalia, California.

*Growth*

Habit: Bushy; upright; many branches.

Growth: Free and vigorous.

Canes: Of medium weight.
Main stems: Green.
*Thorns.*—Few to several; medium length; hooked downward; with long, narrow base.
*Prickles.*—Few.
*Hairs.*—None.
Branches: Bright green.
*Thorns.*—Several; of medium length; hooked downward; with long, narrow base.
*Prickles.*—None to few.
*Hairs.*—None.
New shoots: Bright green.
*Thorns.*—Few to several; of medium length; hooked downward; with long, narrow base.
*Prickles.*—None.
*Hairs.*—None.

The following is claimed:

A new and distinct variety of floribunda rose plant, substantially as herein shown and described, of the bush-type, outdoor variety and which may be utilized as a garden rose or a hedge rose, characterized by its hardy, vigorous growth habit, its glossy foliage, and the deep red color of its abundant flowers, which flowers are borne upright on wiry, stiff stems, the open flowers looking somewhat like carnations of the broad petaled type and the nearly heart-shaped petals of the flowers being somewhat waved to give the flowers a more double appearance, the medium-sized, moderately thick, satiny petals being arranged regularly, with the newly opened flower a bright red color and the flower opened for three days shading from bright rose red in cool weather to deep pink in warm weather.

No references cited.